United States Patent [19]
Dutra

[11] 4,067,719
[45] Jan. 10, 1978

[54] O-ARYL N-PHOSPHONOMETHYLGLYCINONITRILES AND THE HERBICIDAL USE THEREOF

[75] Inventor: Gerard A. Dutra, Ladue, Mo.

[73] Assignee: Monsanto Company, St. Louis, Mo.

[21] Appl. No.: 750,327

[22] Filed: Dec. 13, 1976

[51] Int. Cl.$^2$ ............................ A01N 9/36; C07F 9/32
[52] U.S. Cl. ............................................ 71/86; 71/87; 260/340.5 R; 260/465.5 R; 260/970
[58] Field of Search ............ 260/940, 465.5 R, 340.5; 71/86, 87

[56] References Cited

U.S. PATENT DOCUMENTS 4,008,296  2/1977  Barton .................................. 260/940

Primary Examiner—Richard L. Raymond
Attorney, Agent, or Firm—Arnold H. Cole; Donald W. Peterson

[57] ABSTRACT

O-aryl N-phosphonomethylglycinonitriles are described as well as a process for producing same. These phosphonomethyl substituted glycinonitriles are useful as herbicides.

57 Claims, No Drawings

O-ARYL N-PHOSPHONOMETHYLGLYCINONITRILES AND THE HERBICIDAL USE THEREOF

This invention relates to novel O-aryl N-phosphonomethylglycinonitriles which are useful as herbicides. This invention further relates to herbicidal compositions and to herbicidal methods employing said O-aryl N-phosphonomethylglycinonitriles.

According to U.S. Pat. No. 3,923,877, N-phosphonomethylglycine can be produced by reacting a dihydrocarbylphosphite with 1,3,5-tricyanomethyl-hexahydro-1,3,5-triazine in the presence of a catalyst, such as hydrogen halide, a Lewis acid, a carboxylic acid halide or a carboxylic acid anhydride and then hydrolyzing the resultant product. Yields by this process are extremely low. The patent states that the reaction takes place between the phosphite and the triazine to produce an intermediate ester of N-phosphonomethylglycinonitrile. The convenient esters according to the patent are aliphatic of 1 to 6 carbon atoms or phenyl-substituted aliphatic groups such as benzyl and preferable alkyl of 1 to 6 carbon atoms. These esters are hydrolyzed to yield N-phosphonomethylglycine, a post-emergent herbicide. It has been found that the O,O-diethyl N-phosphonomethylglycinonitrile produced in accordance with the process of the reference had no post-emergent herbicidal activity at 4.48 kg/hectare and no pre-emergent herbicidal activity at 5.60 kg/hectare.

It has now been discovered that O,O-diaryl N-phosphonomethylglycinonitriles can be produced by the reaction of a diaryl phosphite with 1,3,5-tricyanomethyl-hexahydro-1,3,5-triazine without the need of any catalyst. It has further been discovered that these glycinonitriles so produced, as well as the corresponding mono-aryl esters produced by mild hydrolysis of the diester compounds have pre- and post-emergent herbicidal activity which is totally unexpected due to the inactivity of the diethyl N-phosphonomethylglycinonitrile.

The N-phosphonomethylglycinonitriles of this invention are compounds having the formula

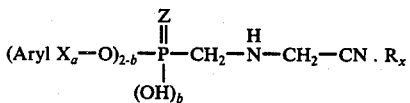

wherein Aryl is selected from phenyl, naphthyl or biphenylyl, each X is a substituent on said Aryl selected from halogen, alkyl of 1 to 4 carbons, alkoxy and alkylthio of 1 to 3 carbons, alkoxycarbonyl of 2 to 3 carbon atoms, methylenedioxy, cyano, trifluoromethyl or nitro, Z is oxygen or sulfur, $a$ is an integer from zero to 3, $b$ is an integer from zero to 1, R is a strong acid capable of forming a salt with the amino group, and $x$ is zero or 1, provided that $x$ must be zero when $b$ is 1.

According to the above proviso, the strong acid salts are only formed with a diester. When a strong acid is added to a monoester (see formula IV below) the single aryl ester group may be hydrolyzed from the molecule.

The N-phosphonomethylglycinonitriles of formula I wherein $x$ and $b$ are zero are produced by forming an admixture consisting essentially of a phosphorous acid ester of the formula

wherein X, Z and $a$ are as above defined and 1,3,5-tricyanomethylhexahydro-1,3,5-triazine (also named N-methyleneglycinonitrile trimer) of the formula

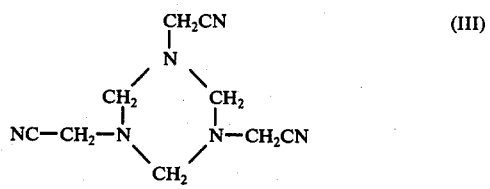

and heating said admixture to a temperature sufficiently elevated to initiate the reaction and maintaining a temperature sufficient to sustain the reaction of the phosphorous acid ester with the triazine to produce said N-phosphonomethylglycinonitrile I.

Although a solvent is not necessary in the process of the instant invention, it is sometimes desirable to employ a solvent for convenience and ease of reaction. A solvent is also useful to control the temperature of the reaction. The solvent employed is one in which the triazine is soluble and which does not react with either of the reactants. Such inert solvents include acetonitrile, ethyl acetate, tetrahydrofuran and the like.

It has been found that the reaction temperature can be as low as about 25° C to about 110° C. Higher temperature can be employed but no commensurate advantages are obtained thereby since the reaction is essentially complete by the time the temperature reaches about 85° C.

As can be seen from the above formulas II and III, the ratio of the phosphorous acid ester to triazine should be 3 to 1 for best results. Higher or lower ratios could be employed but no commensurate advantages are obtained thereby, since at higher ratios excess phosphorous acid ester would have to be separated and at lower ratios of ester to triazine by-product formation is possible.

The reaction is generally conducted at atmospheric pressure for economy. However, higher or lower pressures can be employed but no commensurate advantages are obtained thereby.

To produce compounds of formula I wherein $b$ is 1 and $x$ is 0, that is compounds of the formula

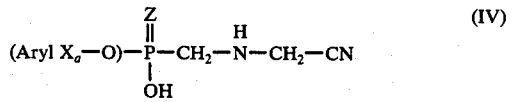

wherein X, Z and $a$ are as above defined, one merely forms a solution of a compound of the formula

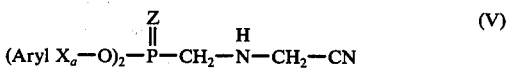

wherein X, Z and $a$ are as above defined, in a solvent containing a small amount of water and maintaining the solution at ambient temperatures at which one of the (Aryl X$_a$—O) groups is hydrolyzed. The solvent preferred for the hydrolysis is acetone. The desired material is isolated by standard procedures such as fractional crystallization or vacuum evaporation of the solvent and other volatile hydrolysis products wherein the desired material is obtained as a residue.

To produce the compounds of formula I wherein $b$ is zero and $x$ is 1, i.e., compound of the formula

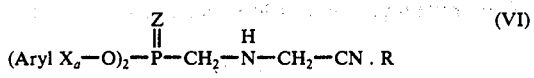 (VI)

wherein X, Z and $a$ have the above-defined meanings, one dissolves a compound of formula V in an anhydrous solvent such as chloroform and adds to said solution a strong acid, either in a solvent or in some instances the acid is added per se, with stirring at ambient temperature for a time sufficient to allow said compound of formula V and said acid to react to produce the compound of formula VI. In many instances the desired product precipitates in crystalline form from the reaction solution. In other instances a 50—50 volume mixture of chloroform and diethyl ether is added to induce product crystallization or to separate it from the reaction solution as an oil.

The compounds of formula VI are salts of the diester of formula V and can also be represented by the formula

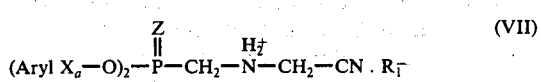 (VII)

wherein X, Z and $a$ are as above-defined and $R_1$ is the anion of the strong acid.

Illustrative of the groups substituted on the phenyl, napthyl or biphenylyl and represented by X are, for example, halogen such as chlorine, fluorine and bromine; alkyl such as methyl, ethyl, propyl and butyl; alkoxy such as methoxy, ethoxy and propoxy; alkylthio such as methylthio, ethylthio and propylthio; as well as methylenedioxy, cyano, trifluoromethyl and nitro. It is apparent from the formula that the groups represented by X can be the same or different on the same aryl ring.

The strong acids which are useful in preparing the strong acid salts of formula I, VI and VII are those having a $pK_a$ in water of 2.5 or less and include, for example, p-toluenesulfonic acid, p-chlorobenzenesulfonic acid, trichloroacetic acid, oxalic acid, fluoboric acid, hydrogen chloride, hydrogen bromide, hydriodic acid, trifluoroacetic acid, pentafluoropropionic acid, heptafluorobutyric acid, trifluoromethanesulfonic acid, nitric acid, sulfuric acid, phosphoric acid, trichloromethanephosphonic acid, perchloric acid, methanesulfonic acid and the like.

In preparing the strong acid salts of formulas I, VI and VII it is preferred to employ the diester of the phosphonic acid and the strong acid in equal molar ratios for ease of isolation of the strong acid salt. Higher or lower ratios of ester to acid can be employed although isolation of the product is made more difficult because of the presence of an excess of one of the reactants.

The compounds represented by formula I are useful as herbicides for both pre-emergent and post-emergent application.

The following general procedures show the preferred methods of producing the various compounds of this invention.

The diaryl esters of formula V are preferably produced by one of the following two methods.

A. An acetonitrile solution (50 ml.) of 1,3,5-tricyanomethyl-hexahydro-1,3,5-triazine (3.4 g., 0.0167 mole) and the diarylphosphite (.050 mole) are admixed in a reaction vessel and heated from 45° C to 85° C for from 1 to 90 hours until all of the phosphite or triazine is consumed as determined by n.m.r. analysis. If the n.m.r. spectral analysis indicates that no impurities are present, the product is isolated by vacuum concentration. If impurities are present, the product is isolated and purified by crystallization or chromatographically. In some instances, the diester product may be difficult to isolate in a highly pure form because hydrolysis occurs during the attempted isolation.

B. A mixture of a diaryl phosphite (0.05 mole) and 1,3,5-tricyanomethyl-hexahydro-1,3,5-triazine (3.4 g., 0.0167 mole) is charged into a reaction vessel and heated to from 60° to 100° C for from 20 minutes to one hour, until all of the phosphite or triazine has been consumed as determined by n.m.r. spectral analysis. The products are purified by crystallization or chromatography.

The monoaryl esters of N-phosphonomethylglycinonitrile are prepared by dissolving the diaryl ester in acetone containing a small amount of water (usually about 2% by weight water) and stirring the reaction mixture for from 18 to 72 hours. The mono esters are usually crystalline and are collected by filtration, washed with acetone and air dried.

The strong acid salts of the diaryl esters are preferably prepared by the following general procedure. A solution of the strong acid (or the acid per se) (0.01 mole) is added dropwise to a chloroform solution of the diester at ambient temperature and allowed to stand. If crystals form they are collected by filtration, washed with a 50 volume percent chloroform-ether mixture and air dried. Otherwise a 50 volume percent chloroform-ether mixture is added to cause the salt to crystallize or to come out of solution as an oil.

The following experiments serve to further illustrate the invention, all parts being parts by weight unless otherwise specifically set forth.

EXAMPLE 1

Di(p-chlorophenyl)phosphite (23.32 g., 78% pure, 0.06 mole) and 1,3,5-tricyanomethyl-hexahydro-1,3,5-triazine (4.08 g., 0.02 mole) were mixed in a reaction vessel at ambient temperature and the mixture heated to 100° C for 20 minutes to give O,O-di(p-chlorophenyl) N-phosphonomethylglycinonitrile in 100% yield, 27 g., $n_D^{21} = 1.5747$.

EXAMPLE 2

An acetonitrile solution (10 ml.) of di(3,4-dimethylphenyl)phosphite (8.7 g., .03 mole) was added to an acetonitrile solution (50 ml.) of 1,3,5-tricyanomethyl-hexahydro-1,3,5-triazine (2.04 g., 0.01 mole) and the mixture was heated at 55° C for 90 hr. Filtration of the solid present and evaporation of the solvent gave a burgundy colored oil which by n.m.r. analysis contained the desired product and the aminal of this product. Chromatography of the oil (8.0 g.) over silica gel (450 g.) with 50% cyclohexane/50% ethyl acetate (60 ml. fractions) gave O,O-di(3,4-dimethylphenyl) N-phosphonomethylglycinonitrile in fractions 30–41 which melted at 61°–64° C after removal of the solvent. The solid was recrystallized from carbon tetrachloride-isooctane, m.p. 63°–66° C, 3.1 g. obtained (40% yield).

Fractions 20–25 from the chromatographic column, upon evaporation of the solvent, gave 1.62 g. of an oil, $n_D^{22} = 1.5387$. Crystallization of this oil from carbon tetrachloride-isooctane afforded a white solid identified as N,N'-methylenebis-[O,O-di(3,4-dimethylphenyl) N-phosphonomethylglycinonitrile].

EXAMPLE 3

A stirred mixture of 0.02 mole di(p-methylthiophenyl)phosphite and 0.0067 mole of 1,3,5-tricyanomethyl-hexahydro-1,3,5-triazine was heated to 80° C for 1.0 hr. resulting in a dark red brown oil. Half of the sample was then placed in the refrigerator for 8 days giving a semi-solid mass. The sample was then recrystallized from 70 ml. carbon tetrachloride to give a pink solid. The solid was dissolved in 100 ml. hot carbon tetrachloride and filtered through celite covered with 5.0 g. silica gel. The filtrate was concentrated to 50 ml. and put in the refrigerator overnight. The suspension was filtered to give 1.8 g. (45%) of a white solid identified as O,O-di(p-methylthiophenyl) N-phosphonomethylglycinonitrile having a melting point of 64°–65° C and the following analysis.

Calc'd: C: 51.8; H: 4.9; N: 7.1; Found: C: 51.7; H: 4.9; N: 7.1.

EXAMPLE 4

A solution of di(o-methoxyphenyl)phosphite (8.05 g., 91% pure, .025 mole) and 1,3,5-tricyanomethyl-hexahydro-1,3,5-triazine (1.7 g., 0.0083 mole) was heated at 55° C for 73 hours and then filtered. The filtrate was concentrated to a dark brown oil (9.6 g.). The oil (5.8 g.) was adhered on 8 grams silica gel and extracted with 80 ml. ethyl acetate. The ethyl acetate solution was concentrated and the resulting oil adhered on 4.0 g. silica gel. This silica gel was extracted with 70 ml. of ethyl acetate and the solution concentrated under vacuum to yield a pale yellow oil, $n_D^{22} = 1.5542$. The yellow oil was found to be O,O-di(o-methoxyphenyl) N-phosphonomethylglycinonitrile containing a small amount of o-methoxyphenol.

EXAMPLE 5

A solution of 1,3,5-tricyanomethyl-hexahydro-1,3,5-triazine (13.6 g., 0.066 mole) and diphenyl phosphite (46.8 g., 0.2 mole) in acetonitrile (100 ml.) was heated at 55° C for 48 hours. The n.m.r. of the crude reaction mixture indicated complete conversion to O,O-diphenyl N-phosphonomethylglycinonitrile. The acetonitrile was removed in vacuo to yield 57 g. (94.4%) of a viscous black oil. The oil was dissolved in chloroform, 114 g. of silica gel added and the mixture evaporated to dryness in vacuo. The product-impregnated silica gel was then placed on a column containing a slurry of chloroform and silica gel (200 g.) and eluted until the product was no longer detected in the eluent by n.m.r. The chloroform eluents were concentrated, dissolved in methylene chloride and washed twice with cold 5% KOH (100 ml.), then with water. The methylene chloride layer was dried over MgSO$_4$, filtered and evaporated leaving 37.9 g. of a light yellow oil which solidified on standing. The solid had a melting point of 64°–67.5° C and was identified as O,O-diphenyl N-phosphonomethylglycinonitrile, obtained in 75% yield.

EXAMPLE 6

An acetonitrile solution (100 ml.) of di(m-tolyl)phosphite (10.7 g., .04 mole) and 1,3,5-tricyanomethyl-hexahydro-1,3,5-triazine (2.72 g., .0133 mole) was heated to 50° C for 3 days. The solution turned a wine red color, and the solvent was evaporated leaving 12.4 g. of a red oil (92.4% recovery). The oil (9.0 g.) was chromatographed over silica gel eluted with 60% cyclohexane/40% ethyl acetate with 60 ml. fractions taken. Fr. 45–63 were pure O,O-di(m-tolyl) N-phosphonomethylglycinonitrile, $n_D^{25} = 1.5467$ (1.25 g., 14% yield) which had the following analysis.

Calc'd: C: 61.81; H: 5.80; N: 8.48; Found: C: 61.75; H: 5.81; N: 8.41.

Fractions 28–40 from the chromatograph were evaporated in vacuo to yield a solid having a melting point of 113°–114° C and identified as N,N'-methylene bis-[O,O-di(m-tolyl) N-phosphonomethylglycinonitrile.

EXAMPLE 7

A solution of di(m-nitrophenyl)phosphite (15.2 g., 83% pure, .0392 mole) and 1,3,5-tricyanomethyl-hexahydro-1,3,5-triazine (2.66 g., .013 mole) in acetonitrile was heated to 50° C for 20 hours. N.m.r. analysis indicated complete reaction. The solution was filtered and the solvent removed in vacuo leaving 13 g. of an amber oil identified as O,O-di(m-nitrophenyl) N-phosphonomethylglycinonitrile which gave the following analysis.

Calc'd: C: 45.93; H: 3.34; N: 14.28; Found: C: 45.80; H: 3.39; N: 14.27.

EXAMPLE 8

Di(p-methoxyphenyl)phosphite (0.05 mole, 15.63 g., 94% pure) and 1,3,5-tricyanomethyl-hexahydro-1,3,5-triazine (3.4 g., .0167 mole) were dissolved in acetonitrile and the solution heated to reflux for 1 hour. The solvent was evaporated off in vacuo yielding a dark pink oil (19.0 g.). This oil (5 g.) was subjected to high pressure liquid chromatography using a mixture of cyclohexane and ethyl acetate (40/60 vol. %) to recover 4.1 g of O,O-di(p-methoxyphenyl) N-phosphonomethylglycinonitrile as an oil, $n_D^{25} = 1.5541$, 82% yield.

EXAMPLE 9

A mixture of 1,3,5-tricyanomethyl-hexahydro-1,3,5-triazine (2.04 g., .01 mole) and di(p-fluorophenyl)phosphite (8.8 g., 91.6% pure, 0.03 mole) in acetonitrile (50 ml.) was heated to 55° C for 70 hours. The reaction mixture was then filtered and the solvent removed in vacuo to yield a brown oil, $n_D^{25} = 1.5270$, which was 92% pure O,O-di(p-fluorophenyl N-phosphonomethylglycinonitrile.

EXAMPLE 10

Di(m-chlorophenyl)phosphite (9.93 g., 91.5% pure, 0.03 mole) dissolved in acetonitrile (20 ml.) was added to 1,3,5-tricyanomethyl-hexahydro-1,3,5-triazine (2.04 g., 0.01 mole) dissolved in acetonitrile (50 ml.), and the mixture was heated to 55° C for 70 hours. The acetonitrile was removed in vacuo leaving a light pink oil, $n_D^{25} = 1.5656$, which was 92% pure O,O-di(m-chlorophenyl) N-phosphonomethylglycinonitrile.

The following compounds can also be prepared by the above procedures:

O,O-di(p-cyanophenyl) N-phosphonomethylglycinonitrile

O,O-di)p-biphenylyl) N-phosphonomethylglycinonitrile

EXAMPLE 11

The diester (4.0 g., 0.099 mole) prepared in Example 10 was dissolved in 100 ml. of 2% aqueous acetone and the solution stirred at ambient temperature for 6 days during which time a solid formed. The solids were collected, washed with acetone and dried to yield 1.55 g. (60%) O-m-chlorophenyl N-phosphonomethylglycinonitrile as a solid having a melting point of 181°–182° C and having the following analysis.

Calc'd: C: 41.5; H: 3.9; N: 10.8; Found: C: 41.5; H: 3.9; N: 10.8.

EXAMPLE 12

The diester prepared in Example 9 (2.38 g., .069 mole) was dissolved in 2% aqueous acetone (100 ml.) and stirred at ambient temperature for 3 days. The resulting slurry was filtered and the solids washed with acetone giving 0.87 g. of a tan solid having a melting point of 258°–262° C. The mother liquor was allowed to stand for 6 weeks and the resulting solids were collected and washed with acetone to give an additional 0.8 grams of material having the same melting point which was identified as O-p-fluorophenyl N-phosphonomethylglycinonitrile in a 98% yield and having the following analysis.

Calc'd: C: 44.3; H: 4.1; N: 11.5; Found: C: 44.3; H: 4.2; N: 11.5.

EXAMPLE 13

O,O-Diphenyl N-phosphonomethylglycinonitrile (1.51 g., 0.005 mole) was stirred in 50 ml. of 2N hydrochloric acid with heating until all of the material dissolved (2 hours). An amber oil was noted in the bottom of the flask and found to be phenol. The flask was cooled to room temperature and the hydrochloric acid solution washed twice with methylene chloride (25 ml.) to remove any starting material and the phenol formed in the reaction. The hydrochloric acid solution was then cooled in an ice bath during which time crystals began to form. The crystals were collected, washed with cold water and air dried. The crystals were identified as O-phenyl N-phosphonomethylglycinonitrile and had no distinct melting point. The crystals gave the following analysis.

Calc'd: C: 47.79; H: 4.90; N: 12.39; Found: C: 47.52 H: 4.93; N: 12.12.

EXAMPLE 14

O,O-di(m-tolyl) N-phosphonomethylglycinonitrile (4.0 g., 0.012 mole) was dissolved in acetone (50 ml.) containing water (1 ml.) and stirred for 60 days at ambient temperature. Three crops of crystals were obtained. The first two crops of crystals had a melting point of 161°–166° C and were determined to be impure. The third crop had a melting point of 179°–179.5° C and were found to be analytically pure O-m-tolyl N-phosphonomethylglycinonitrile, which was obtained in 53% yield and had the following analysis.

Calc'd: C: 50.0; H: 5.5; N: 11.7; Found: C: 50.0; H: 5.5; N: 11.7.

EXAMPLE 15

O,O-di(m-nitrophenyl) N-phosphonomethylglycinonitrile (3.15 g., .008 mole) was dissolved in acetone (50 ml.) and water (1 ml.) and stirred at room temperature for 16 hours. Solids formed which were collected and washed with acetone yielding 1.1 grams (51%) of a material identified as O-m-nitrophenyl N-phosphonomethylglycinonitrile having a melting point of 174°–176° C with decomposition and having the following analysis.

Calc'd: C: 40.0; H: 3.4; N: 15.6; Found: C: 40.0; H: 3.4; N: 15.5.

EXAMPLE 16

An acetonitrile solution (100 ml.) of di(m-trifluorotolyl)phosphite (11.64 g., 0.0314 mole) and 1,3,5-tricyanomethyl-hexahydro-1,3,5-triazine (2.15 grams, 0.0105 mole) was heated at 50° C overnight. The acetonitrile was evaporated off under vacuum and solids began forming. The residue material was dissolved in acetone (50 ml.) and water (1 ml.) and stirred overnight at ambient temperature during which time solids formed. The solids were collected and washed with acetone yielding 3.5 grams (39.5%) of a white solid having a melting point of 195°–196° C and identified as O-m-trifluorotolyl N-phosphonomethylglycinonitrile and having the following analysis.

Calc'd: C: 40.8; H: 3.4; N: 9.5; Found: C: 41.0; H: 3.5; N: 9.7.

EXAMPLE 17

O,O-di(p-chlorophenyl) N-phosphonomethylglycinonitrile (9.0 g., 0.024 mole) was dissolved in acetone (50 ml.) and water (1 ml.) and stirred at room temperature for 2 days. A solid formed which was collected and weighed 2.35 grams. The solid had a melting point of 170° C with decomposition and was identified as O-p-chlorophenyl N-phosphonomethylglycinonitrile. The mother liquor was allowed to stand for several weeks and an additional 0.85 grams was collected. The total yield of the product was 3.2 grams (51% yield).

EXAMPLE 18

21 g. of a solution containing 83.8% by weight of di(3-methyl-4-nitrophenyl)phosphite (0.05 mole) and 1,3,5-tricyanomethyl-hexahydro-1,3,5-triazine (3.4 g., 0.0167 mole) were dissolved in 100 ml. of acetonitrile and heated to 70° C for 1 hour. The acetonitrile solvent was then removed under vacuum and the residue dissolved in 50 ml. of acetone containing 1 ml. of water and stirred at ambient temperature. The crystals (4.3 g., 30% yield) were identified as O-(3-methyl-4-nitrophenyl) N-phosphonomethylglycinonitrile, having a melting point of 181°–182° C. The material had the following analysis.

Calc'd: C: 42.1; H: 4.2; N: 14.7; Found: C: 42.2; H: 4.3; N: 14.7.

EXAMPLE 19

O,O-di(p-methoxyphenyl) N-phosphonomethylglycinonitrile (3.0 g., 0.0082 mole) was dissolved in acetone (50 ml.) and water (1 ml.) and stirred at ambient temperature for three months. During this period solids formed. The solids were removed by filtration, washed with acetone and dried. Solid material was identified as O-p-methoxyphenyl N-phosphonomethylglycinonitrile and had a melting point of 185°–195° C with decomposition. The material gave the following analysis.

Calc'd: C: 46.9; H: 5.1; N: 11.0; Found: C: 47.1; H: 5.2; N: 10.8.

EXAMPLE 20

Di(o-chlorophenyl)phosphite (19.5 g., 80% by weight, 0.05 mole) was added to an acetonitrile solution (50 ml.) of 1,3,5-tricyanomethyl-hexahydro-1,3,5-triazine (3.4 g., 0.01640 mole) and heated to 70° C for 2 hours. A 15 ml. portion of the reactant solution was concentrated and dissolved in acetone (50 ml.) and water (1 ml.) and stirred overnight during which time solids formed. The solids were collected, washed with acetone and dried, yielding 3.2 grams (82% yield) of a material identified as O-o-chlorophenyl N-phosphonomethylglycinonitrile having a melting point of 170°–171° C and the following analysis.

Calc'd: C: 41.5; H: 3.9; N: 10.8; Found: C: 41.4; H: 3.9; N: 10.7.

EXAMPLE 21

O,O-di(p-fluorophenyl) N-phosphonomethylglycinonitrile (2.38 g., 0.069 mole) was stirred in a 50 volume percent mixture of carbon tetrachloride and methylene chloride, filtered and methanesulfonic acid (0.67 grams, 0.069 mole) was added. The solution was allowed to stand overnight, the crystals formed were collected by filtration and washed with carbon tetrachloride to give 2.68 grams of a white crystalline material identified as the methanesulfonic acid salt of O,O-di(p-fluorophenyl) N-phosphonomethylglycinonitrile. This salt had a melting point of 132°–132.5° C and gave the following analysis.

Calc'd: C: 44.2; H: 4.0; N: 6.5; S: 7.4; Found: C: 44.0; H: 4.0; N: 6.6; S: 7.5.

EXAMPLE 22 p-Toluenesulfonic acid (1.9 gram, 0.01 mole) was refluxed in benzene (100 ml.) and the water present removed by azeotroping with benzene. This benzene solution was added to a benzene-methylene chloride solution (50/50 volume percent, 100 ml.) of O,O-diphenyl N-phosphonomethylglycinonitrile (3.02 grams, 0.1 mole). The mixture was stirred for one minute at room temperature, during which crystallization occurred. The resulting slurry was stirred at room temperature overnight and then filtered to yield a white solid, identified as the p-toluenesulfonic acid salt of O,O-diphenyl N-phosphonomethylglycinonitrile (4.38 grams, 92.4% yield), having a melting point of 152°–153° C. The compound gave the following analysis.

Calc'd: C: 55.7; H: 4.9; N: 5.9; Found: C: 55.4; H: 4.9; N: 5.7.

EXAMPLE 23

A chloroform solution of p-chlorobenzenesulfonic acid (1.92 grams, 0.01 mole) was added to a chloroform solution of O,O-diphenyl N-phosphonomethylglycinonitrile (3.0 grams, 0.01 mole). The mixture was stirred and after 10 minutes crystallization commenced. The slurry was then stirred overnight, filtered and the solids washed with chloroform leaving 4.0 grams of a while solid (81%), melting point 149°–151° C; identified as the p-chlorobenzenesulfonic acid salt of O,O-diphenyl N-phosphonomethylglycinonitrile, having the following analysis.

Calc'd: C: 51.0; H: 4.1; N: 5.7; Found: C: 50.7; H: 4.1; N: 5.7.

EXAMPLE 24

A chloroform solution (20 ml.) of trichloroacetic acid (1.63 grams, 0.01 mole) was added to a chloroform solution (100 ml.) of O,O-diphenyl N-phosphonomethylglycinonitrile (3.0 grams, 0.01 mole) and stirred overnight at room temperature. Crystallization could not be induced and the solvents were removed in vacuo leaving a light yellow oil, 3.75 grams (80%) $n_D^{25}$ = 1.5410, identified as the trichloroacetic acid salt of O,O-diphenyl N-phosphonomethylglycinonitrile, having the following analysis.

Calc'd: C: 43.9; H: 3.5; N: 6.0; Found: C: 43.9; H: 3.5; N: 5.9.

EXAMPLE 25

An acetone solution (25 ml.) of oxalic acid dihydrate (1.26 grams, 10 mole) was added to an acetone solution of O,O-diphenyl N-phosphonomethylglycinonitrile (3.02 grams, 10 mole). After 10 minutes, the salt started crystallizing from the solution. The solution was stirred overnight, cooled and the solids (1.9 grams) were collected and washed with acetone. A second crop was obtained by concentrating the mother liquor, 0.8 gram. The yield was 2.7 grams, 69%, melting point 165° C dec. The crystals were identified as the oxalic acid salt of O,O-diphenyl N-phosphonomethylglycinonitrile, and had the following analysis.

Calc'd: C: 52.1; H: 4.4; N: 7.1; Found: C: 52.1; H: 4.4; N: 7.1.

EXAMPLE 26

An ether solution of perchloric acid was added to a chloroform-ether solution of O,O-diphenyl N-phosphonomethylglycinonitrile (3.0 grams, 10 mole). The perchlorate salt slowly crystallized as white prisms. The solids, identified as the perchloric acid salt of O,O-diphenyl N-phosphonomethylglycinonitrile, were collected and washed with ether-chloroform to give 0.73 gram, 18% yield, melting point 166°–168° C. The salt had the following analysis.

Calc'd: C: 44.7; H: 4.0; N: 7.0; Found: C: 44.8; H: 4.0; N: 7.0.

EXAMPLE 27

A chloroform-methanol solution of trichloromethane phosphonic acid (1.99 grams, 0.01 mole) was added to a chloroform solution of O,O-diphenyl N-phosphonomethylglycinonitrile (3.0 grams, 10 mole). After 10 minutes, ether was added, and no crystals formed. Petroleum ether was then added until just before the cloud point. After 10 minutes, crystals began to form, and it was allowed to stand an additional 10 minutes. The crystals were collected in two crops, 2.9 grams, 58% yield, melting point 145°–146° C. The crystals were identified as the trichloromethane phosphonic acid salt of O,O-diphenyl N-phosphonomethylglycinonitrile, and had the following analysis.

Calc'd: C: 38.3; H: 3.4; N: 5.6; Found: C: 38.3; H: 3.5; N: 5.6.

EXAMPLE 28

An ether solution of fluoboric acid was added to a chloroform-ether solution of O,O-diphenyl N-phosphonomethylglycinonitrile (3.0 grams, 10 mole). The solution was stirred overnight, the solids were filtered, washed with ether-chloroform (50/50) leaving white crystals, 1.1 grams, 28% yield, melting point 156°–158° C, identified as the fluoboric acid salt of O,O-diphenyl N-phosphonomethylglycinonitrile, having the following analysis.

Calc'd: C: 46.2; H: 4.1; N: 7.2; Found: C: 46.0; H: 4.2; N: 7.2.

EXAMPLE 29

Gaseous hydrogen bromide was bubbled into a chloroform solution of O,O-diphenyl N-phosphonomethylglycinonitrile (3.0 grams, 10 mole). The solution was allowed to stand overnight as the hydrobromide crystallized. The crystals were collected and washed with ether, leaving 3.0 grams, 78% yield, identified as the hydrogen bromide salt of O,O-diphenyl N-phosphonomethylglycinonitrile, having the following analysis.

Calc'd: C: 47.0; H: 4.2; N: 7.3; Found: C: 47.1; H: 4.3; N: 7.4.

EXAMPLE 30

A 57% solution of hydriodic acid (2 ml.) was added to a chloroform solution of O,O-diphenyl N-phosphonomethylglycinonitrile (3.0 grams, 10 mole). The solution became cloudy and turned golden color. After two hours no solids formed, so ether was added to the cloud point and crystallization commenced. The solution was stirred an additional hour and the solids, identified as the hydriodic acid salt of O,O-diphenyl N-phosphonomethylglycinonitrile, were collected as light yellow plates, melting point 163°–164° C, 2.4 grams, 56% yield. The salt had the following analysis.

Calc'd: C: 41.9; H: 3.8; I: 29.5; Found: C: 41.8; H: 3.8; I: 29.3.

EXAMPLE 31

Trifluoroacetic acid (1.14 grams, 10 mole) was added to a chloroform solution of O,O-diphenyl N-phosphonomethylglycinonitrile (3.0 grams, 10 mole). The solution was stirred overnight and the solvent evaporated in vacuo leaving a light yellow oil, 4.0 grams, 96% yield, $n_D^{25}$ = 1.5172, identified as the trifluoroacetic acid salt of O,O-diphenyl N-phosphonomethylglycinonitrile.

EXAMPLE 32

Trifluoromethanesulfonic acid (1.50 grams, 10 mole, fumes) was added to a chloroform solution of O,O-diphenyl N-phosphonomethylglycinonitrile (3.0 grams, 10 mole). The reaction was stirred at room temperature for two hours, and ether was added to the cloud point. The product crystallized. After standing for one hour, the solids were collected and washed with chloroform-ether (50%) to yield 3.8 grams, 84% yield, melting point 119°–120° C, identified as the trifluoromethanesulfonic acid salt of O,O-diphenyl N-phosphonomethylglycinonitrile, having the following analysis.

Calc'd: C: 42.5; H: 3.6; N: 6.2; Found: C: 42.7; H: 3.6; N: 6.2.

EXAMPLE 33

To a chloroform solution of O,O-diphenyl N-phosphonomethylglycinonitrile (15.1 grams, .05 mole) was added methanesulfonic acid (5.0 grams, 0.051 mole) and the solution stirred for 2 hours at ambient temperatures. A solid precipitated and was collected, washed with ether and dried. The solid weighed 15.90 grams and was identified as the methanesulfonic acid salt of O,O-diphenyl N-phosphonomethylglycinonitrile, having a melting point of 147°–150° C. The yield of the salt was 82.1%. The salt had the following analysis.

Calc'd: C: 44.2; H: 4.0; N: 6.5; S: 7.4; Found: C: 44.0; H: 4.0; N: 6.6; S: 7.5.

EXAMPLE 34

An ether solution (10 ml.) of nitric acid (70% by weight, 0.9 g., .01 mole) was added to a chloroform solution (100 ml.) containing O,O-diphenyl N-phosphonomethylglycinonitrile (3.0 g., 0.01 mole). No clouding occurred. Additional diethyl ether was added, and then isooctane (20 milliliters) at which time solids began crystallizing out of the solution. The mixture was stirred for 1 hour at ambient temperatures, the crystals collected, washed with chloroform and air-dried. The crystals weighed 2.66 grams and were identified as the nitric acid salt of N,N-diphenyl N-phosphonomethylglycinonitrile, having a melting point of 116°–116.5° C. The yield was 72% of theory. The salt had the following analysis.

Calc'd: C: 49.32; H: 4.42; N: 11.5; Found: C: 49.2; H: 4.42; N: 11.6.

EXAMPLE 35

To a solution of O,O-diphenyl N-phosphonomethylglycinonitrile (3.0 g., 0.01 mole) in chloroform (100 ml.) was added an ether solution of 98% sulfuric acid (1.01 g., 0.01 mole). Additional chloroform was added and the mixture stirred for two hours. The solids were removed by filtration and washed with chloroform, then ether, and dried to give 3.9 grams of a material identified as the sulfuric acid salt of O,O-diphenyl N-phosphonomethylglycinonitrile, having a melting point of 151°–151.5° C. The salt was obtained in 100% yield and had the following analysis.

Calc'd: C: 45.0; H: 4.28; S: 8.01; Found: C: 44.90; H: 4.27; S: 8.05.

EXAMPLE 36

An ether solution of phosphorus acid (0.01 mole) was added to a chloroform solution of O,O-diphenyl N-phosphonomethylglycinonitrile (3.0 g., 0.01 mole) at ambient temperature with stirring. The solution clouded immediately. An oil was present in the bottom of the flask. After cooling, the solvent was decanted off, evaporated to dryness and dried over anhydrous magnesium sulfate. The solid material was identified as the phosphoric acid salt of O,O-diphenyl N-phosphonomethylglycinonitrile, having a melting point of 74.5°–78.5° C. The salt was obtained in 25% yield and had the following analysis.

Calc'd: C: 45.0; H: 4.5; N: 7.0; Found: C: 44.8; H: 4.6; N: 7.1.

EXAMPLE 37

A heterogeneous solution of O,O-diphenyl N-phosphonomethylglycinonitrile (60.4 g., 0.2 mole) in ethanol (500 ml.) was cooled in an ice bath, and dry HCl was bubbled through. The solution was allowed to stand, ethyl ether was added, and a white solid was collected by suction filtration. More white solid formed on bubbling dry HCl through the ethanol-ether mother liquor at about 0° C., and it was collected and washed with ether. The yield was 62.7 g. (93%) of the hydrochloride salt of O,O-diphenyl N-phosphonomethylglycinonitrile, m.p. 112°-123° C. The salt had the following analysis.

Calc'd: C: 53.19; H: 4.79; N: 8.27; Found: C: 53.51; H: 4.78; N: 8.30.

EXAMPLE 38

Di(2,4,6-trimethylphenyl)phosphite (17.8 g., 0.05 mole) was added to an acetonitrile solution (50 ml.) of 1,3,5-tricyanomethyl-hexahydro-1,3,5-triazine (3.4 g., 0.0164 mole), and the mixture was heated at 80° C. for 18 hours. The black solution which formed was filtered and concentrated to an oil. A portion (7 g.) was chromatographed over silica gel (450 g.) with 70% cyclohexane/30% ethyl acetate (60 ml. fractions) to give 1.0 g. (14%) of O,O-di(2,4,6-trimethylphenyl) N-phosphonomethylglycinonitrile, m.p. 118°-120° C., in fractions 28-40 which crystallized on standing. The product had the following analysis.

Calc'd: C: 65.27; H: 7.04; N: 7.25; Found: C: 65.38; H: 7.07; N: 7.18.

EXAMPLE 39

A solution of the diester product of Example 3 (0.025 mole) in wet acetone (50 ml.) was heated at reflux temperature for 2 hours and then allowed to stand at ambient temperature for 5 days. The suspension was filtered to give an impure pinkish solid (0.9 g.). The filtrate was placed in a stoppered flask and allowed to stand at ambient temperature for 30 additional days. The resulting suspension was filtered, and the solid was washed with acetone (50 ml.). There was obtained 4.5 g. (66%) of O-p-methylthio N-phosphonomethylglycinonitrile as a white solid, m.p. 250°-253° C. (dec.). The product had the following analysis.

Calc'd: C: 44.12; H: 4.81; N: 10.29; Found: C: 44.26; H: 4.86; N: 10.22.

EXAMPLE 40

Diphenyl thiophosphite (8.2 g., 0.0246 mole) and 1,3,5-tricyanomethyl-hexahydro-1,3,5-triazine (1.68 g., 0.00823 mole) were dissolved in acetonitrile (50 ml.) and heated to 60°-65° C. for 2 hours. The resulting oil was chromatographed over silica gel (450 g.) eluted with 60% cyclohexane/40% ethyl acetate (60 ml. fractions) to give 1.6 g. (20%) of O,O-diphenyl N-thiophosphonomethylglycinonitrile, $n_D^{25}$ = 1.5847, in fraction 30. The product had the following analysis.

Calc'd: C: 56.60; H: 4.75; N: 8.80; S: 10.07; Found: C: 56.40; H: 4.80; N: 8.73; S: 10.26.

EXAMPLE 41

An acetonitrile solution (100 ml.) of di(β-naphthyl) phosphite (33.5 g., 0.1 mole) and 1,3,5-tricyanomethyl-hexahydro-1,3,5-triazine (20.4 g., 0.1 mole) was heated to reflux for one hour and then concentrated to a red-brown oil. A 10 g. sample was purified by high pressure liquid chromatography over silica gel, eluting with 60% cyclohexane/40% ethyl acetate (20 ml. fractions). Fractions 45-64 were combined and concentrated, and the resulting oil was crystallized from carbon tetrachloride to give 1.1 g. of O,O-di(β-naphthyl) N-phosphonomethylglycinonitrile as a buff colored solid, m.p. 104°-105° C. The product gave the following analysis.

Calc'd: C: 68.65; H: 4.76; N: 6.96; Found: C: 68.58; H: 4.79; N: 6.92.

EXAMPLE 42

A stirred solution of di(3,4-methylenedioxyphenyl) phosphite (0.05 mole) and 1,3,5-tricyanomethyl-hexahydro-1,3,5-triazine (0.0167 mole) in acetonitrile (75 ml.) was heated to 75° C. for 3 hours and then allowed to stand at ambient temperature overnight. The resulting solution was concentrated to an amber oil. To a chloroform solution (100 ml.) of said oil (7.6 g., 0.02 mole), methanesulfonic acid (1.92 g., 0.02 mole) was added dropwise. After stirring for 15 minutes, ether (200 ml.) was added, and a white solid precipitated. The solid was recrystallized twice from acetone to give 4.6 g. (47%) of the methanesulfonic acid salt of O,O-di(3,4-methylenedioxyphenyl) N-phosphonomethylglycinonitrile, m.p. 135°-136.5° C. The product had the following analysis.

Calc'd: C: 44.45; H: 3.94; N: 5.76; Found: C: 44.26; H: 3.94; N: 5.71.

EXAMPLE 43

A solution of 0.01 mole of the amber oil of Example 42 in wet acetone (70 ml.) was refluxed for 4 days. The amber solution was then allowed to stand for 1 day at ambient temperature. The resulting suspension was filtered to give 1.7 g. of O-(3,4-methylenedioxyphenyl) N-phosphonomethylglycinonitrile as a white solid, m.p. 160°-161° C.

EXAMPLE 44

A stirred solution of di(3,4-dichlorophenyl)phosphite (0.04 mole) and 1,3,5-tricyanomethyl-hexahydro-1,3,5-triazine (0.013 mole) in acetonitrile (40 ml.) was heated to 80° C. and maintained for 18 hours. The resulting solution was concentrated to an oil, wet acetone (80 ml.) was added, and the mixture was refluxed for 80 hours. The resulting suspension was filtered to give a white solid which was washed with acetone (50 ml.) to give 6.3 g. (53%) of O-(3,4-dichlorophenyl) N-phosphonomethylglycinonitrile, m.p. 169°-170° C.

EXAMPLE 45

Di(p-methylthiophenyl)phosphite (30.4 g., 0.082 mole) and 1,3,5-tricyanomethyl-hexahydro-1,3,5-triazine (5.6 g., 0.0275 mole) were heated to 80° C. for 1 hour. The resulting dark red-brown oil was allowed to cool to room temperature and dissolved in carbon tetrachloride (200 ml.). This solution was added to silica gel (30 g.), stirred and filtered, and then again added to silica gel (20 g.) with stirring and filtering. Half of the resulting solution was adhered onto silica gel (12.5 g.) and chromatographed over silica gel (450 g.) eluted with 60% cyclohexane/40% ethyl acetate (60 ml. fractions). Fractions 28-39 were combined to give 1.2 g. of N,N'-methylene-bis-[O,O-di(p-methylthiophenyl) N-phosphonomethylglycinonitrile], $n_D^{22}$ = 1.6151.

EXAMPLE 46

Diphenyl phosphite (234 g., 1.0 mole) was added to an acetonitrile solution (300 ml.) of 1,3,5-tricyanomethyl-hexahydro-1,3,5-triazine (68 g.; 0.333 mole) and heated at 75°-82° C. for 3 hours. The solution was cooled and concentrated in vacuo to give a black oil which was mainly the product of Example 5. A sample of this oil (101 g.) was adhered onto silica gel (which was dissolved in chloroform, more silica gel added and solvent evaporated), and this material was chromatographed over silica gel (1.1 kg.) eluted with chloroform (1 liter fractions). Fractions 13-14 were combined, concentrated and recrystallized from dichloromethane-cyclohexane to give 51 g. of O,O-diphenyl N-phosphonomethylglycinonitrile.

Fractions 11-12 were combined, concentrated to an oil, and solids were removed by filtration. The mother liquor from fractions 11-12 was chromatographed over silica gel (760 g.) eluted with 60% cyclohexane/40% ethyl acetate (100 ml. fractions). Fractions 40-49 were combined and recrystallized from cold carbon tetrachloride to give N,N'-methylenebis-(O,O-diphenyl N-phosphonomethylglycinonitrile), m.p. 98°-99° C. The product gave the following analysis.

Calc'd: C: 60.39; H: 4.90; N: 9.09; Found: C: 60.59; H: 4.79; N: 8.97.

It should be noted that the N,N'-methylenebis compounds which are disclosed in Examples 2, 6, 45 and 46 are also novel and useful. However, such compounds are not a part of the instant invention herein.

EXAMPLE 47

The post-emergence herbicidal activity of various compounds of this invention is demonstrated as follows. The active ingredients are applied in spray form to 14-21 day-old specimens of various plant species. The spray, a water or organic solvent-water solution containing active ingredient and a surfactant (35 parts butylamine salt of dodecylbenzenesulfonic acid and 65 parts tall oil condensed with ethylene oxide in the ratio of 11 moles ethylene oxide to 1 mole tall oil), is applied to the plants in different sets of pans at several rates (kg per hectare) of active ingredient. The treated plants are placed in a greenhouse and the effects are observed and recorded after approximately 2 weeks or approximately 4 weeks. The data is given in Tables I and II.

The post-emergence herbicidal activity index used in Tables I and II is as follows:

| Plant Response | Index |
|---|---|
| 0 - 24% Injury | 0 |
| 25 - 49% Injury | 1 |
| 50 - 74% Injury | 2 |
| 75 - 99% Injury | 3 |
| All Killed | 4 |
| Species not present at time of treatment | * |

In said Tables, WAT indicates weeks after treatment, and the plant species treated are each represented by a code letter as follows:

| | |
|---|---|
| A - Canada Thistle | K - Barnyard Grass |
| B - Cocklebur | L - Soybean |
| C - Velvet Leaf | M - Sugar Beet |
| D - Morning Glory | N - Wheat |
| E - Lambsquarters | O - Rice |
| F - Smartweed | P - Sorghum |
| G - Nutsedge | Q - Wild Buckwheat |
| H - Quackgrass | R - Hemp Sesbania |
| I - Johnson Grass | S - Panicum Spp |
| J - Downy Brome | T - Crabgrass |

TABLE I

| Compound | WAT | kg/h | A | B | C | D | E | F | G | H | I | J | K |
|---|---|---|---|---|---|---|---|---|---|---|---|---|---|
| 1 | 4 | 11.2 | 3 | 4 | 4 | 1 | 4 | 4 | 3 | 2 | 3 | 3 | 3 |
| | 4 | 5.6 | 3 | 3 | 4 | 2 | 4 | 4 | 2 | 1 | 1 | 2 | 3 |
| 2 | 4 | 11.2 | 4 | 4 | 3 | 2 | 4 | 3 | 3 | 2 | 2 | 3 | 4 |
| | 4 | 5.6 | 3 | 3 | 3 | 2 | 4 | 4 | 2 | 1 | 1 | 4 | 3 |
| 3 | 4 | 11.2 | 3 | 3 | 3 | 3 | 4 | 4 | 2 | 3 | 3 | 2 | 3 |
| | 4 | 5.6 | 3 | 4 | 1 | 2 | 4 | 4 | 2 | 2 | 2 | 1 | 2 |
| 4 | 4 | 11.2 | 4 | 4 | 3 | 4 | 4 | 4 | 2 | 2 | 2 | 4 | 3 |
| | 4 | 5.6 | 4 | 3 | 3 | 2 | 3 | 4 | 2 | 1 | 1 | 3 | 4 |
| 5 | 4 | 11.2 | 2 | 4 | 3 | 4 | 4 | 3 | 2 | 2 | 3 | 3 | 4 |
| | 4 | 4.48 | 3 | 4 | 3 | 3 | 4 | 4 | 2 | 1 | 2 | 1 | 3 |
| 6 | 4 | 11.2 | 3 | 4 | 4 | 3 | 4 | 4 | 1 | 2 | 2 | 2 | 3 |
| | 4 | 5.6 | 2 | 4 | 1 | 3 | 4 | 4 | 1 | 1 | 3 | 1 | 3 |
| 7 | 4 | 11.2 | 2 | 3 | 2 | 1 | 4 | 3 | 2 | 1 | 4 | 2 | 2 |
| | 4 | 5.6 | 3 | 2 | 2 | 1 | 3 | 3 | 1 | 1 | 4 | 1 | 3 |
| 8 | 4 | 11.2 | 2 | 4 | 2 | 1 | 4 | 4 | 2 | 3 | 4 | 1 | 3 |
| | 4 | 5.6 | 3 | 3 | 3 | 2 | 4 | 4 | 2 | 2 | 4 | 1 | 3 |
| 9 | 4 | 11.2 | 4 | 4 | 4 | 3 | 4 | 4 | 1 | 3 | 2 | 3 | 4 |
| | 4 | 5.6 | 4 | 4 | 4 | 2 | 4 | 4 | 1 | 3 | 2 | 3 | 4 |
| 10 | 4 | 11.2 | 4 | 4 | 3 | 3 | 4 | 4 | 2 | 3 | 3 | 4 | 4 |
| | 4 | 5.6 | 3 | 3 | 3 | 2 | 4 | 4 | 1 | 2 | 1 | 3 | 4 |
| 11 | 4 | 11.2 | 4 | 4 | 4 | 4 | 4 | 4 | 3 | 3 | 2 | 3 | 4 |
| | 4 | 5.6 | 4 | 4 | 4 | 2 | 4 | 4 | 2 | 3 | 1 | 3 | 4 |
| 12 | 4 | 11.2 | 4 | 4 | 3 | 2 | 4 | 4 | 2 | 3 | 4 | 2 | 4 |
| | 4 | 5.6 | 4 | 4 | 3 | 2 | 4 | 4 | 3 | 3 | 3 | 1 | 4 |
| 13 | 4 | 11.2 | * | 4 | 4 | 4 | 3 | 3 | 3 | 4 | 3 | 4 | |
| | 4 | 4.48 | 3 | * | 3 | 3 | 4 | 2 | 3 | 3 | 3 | 3 | 3 |
| 14 | 4 | 11.2 | 4 | 4 | 4 | 3 | 4 | 4 | 4 | 2 | 2 | 3 | 4 |
| | 4 | 5.6 | 3 | 3 | 3 | 2 | 4 | 4 | 1 | 1 | 2 | 3 | 4 |
| 15 | 4 | 11.2 | 4 | 4 | 4 | 2 | 4 | 4 | 3 | 3 | 4 | 4 | |
| | 4 | 5.6 | 3 | 4 | 0 | 1 | 3 | 4 | 2 | 2 | 4 | 3 | 3 |
| 16 | 4 | 11.2 | 4 | 4 | 3 | 1 | 4 | 4 | 3 | 4 | 4 | 2 | 4 |
| | 4 | 5.6 | 4 | 4 | 2 | 1 | 4 | 4 | 2 | 3 | 4 | 0 | 3 |
| 17 | 4 | 11.2 | 4 | 4 | 4 | 3 | 4 | 4 | 3 | 3 | 5 | 4 | 4 |
| | 4 | 5.6 | 3 | 4 | 4 | 3 | 4 | 4 | 2 | 2 | 4 | 3 | 4 |
| 18 | 4 | 11.2 | 3 | 3 | 3 | 2 | 4 | 4 | 2 | 2 | 3 | 2 | 3 |
| | 4 | 5.6 | 4 | 3 | 2 | 2 | 4 | 4 | 2 | 1 | 3 | 1 | 3 |
| 19 | 4 | 11.2 | 4 | 4 | 4 | 2 | 2 | 2 | 3 | 1 | 3 | 0 | 2 |
| | 4 | 5.6 | 2 | 4 | 1 | 1 | 2 | 2 | 3 | 1 | 1 | 0 | 2 |
| 20 | 4 | 11.2 | 3 | 4 | 2 | 2 | 3 | 4 | 2 | 3 | 3 | 2 | 3 |
| | 4 | 5.6 | 3 | 3 | 1 | 2 | 4 | 4 | 2 | 1 | 3 | 2 | 3 |
| 21 | 4 | 11.2 | 4 | 4 | 3 | 2 | 4 | 4 | 2 | 3 | 4 | 3 | 3 |
| | 4 | 5.6 | 2 | 3 | 3 | 2 | 4 | 4 | 2 | 2 | 2 | 3 | 3 |
| 22 | 4 | 11.2 | 4 | 4 | 4 | 3 | 4 | 4 | 4 | 4 | 4 | 4 | 4 |
| | 4 | 5.6 | 3 | 3 | 4 | 2 | 4 | 4 | 3 | 3 | 3 | 2 | 4 |
| 23 | 4 | 11.2 | 4 | 4 | 4 | 4 | 4 | 4 | 4 | 4 | 2 | 4 | 4 |
| | 4 | 5.6 | 4 | 4 | 4 | 3 | 4 | 4 | 4 | 2 | 3 | 4 | 4 |
| 24 | 4 | 11.2 | 4 | 3 | 4 | 3 | 4 | 4 | 3 | 4 | 3 | 4 | 4 |
| | 4 | 5.6 | 3 | 4 | 4 | 1 | 4 | 4 | 2 | 2 | 1 | 3 | 3 |

TABLE I-continued

| Compound | WAT | kg h | A | B | C | D | E | F | G | H | I | J | K |
|---|---|---|---|---|---|---|---|---|---|---|---|---|---|
| 25 | 4 | 11.2 | 4 | 4 | 4 | 3 | 4 | 4 | 3 | 2 | 1 | 4 | 4 |
|  | 4 | 5.6 | 4 | 4 | 4 | 2 | 4 | 4 | 2 | 1 | 2 | 4 | 3 |
| 26 | 4 | 11.2 | 3 | 4 | 3 | 3 | 4 | 4 | 1 | 1 | 3 | 1 | 3 |
|  | 4 | 5.6 | 2 | 3 | 2 | 2 | 4 | 4 | 1 | 1 | 2 | 2 | 2 |
| 27 | 4 | 11.2 | 3 | 3 | 2 | 4 | 4 | 1 | 1 | 1 | 3 | 3 |  |
|  | 4 | 5.6 | 2 | 3 | 3 | 2 | 4 | 4 | 1 | 1 | 1 | 1 | 2 |
| 28 | 4 | 11.2 | 2 | 4 | 4 | 3 | 4 | 4 | 2 | 1 | 3 | 4 | 4 |
|  | 4 | 5.6 | 3 | 3 | 3 | 2 | 3 | 3 | 1 | 0 | 1 | 1 | 3 |
| 29 | 4 | 11.2 | 3 | 3 | 4 | 2 | 3 | 4 | 2 | 1 | 4 | 2 | 4 |
|  | 4 | 5.6 | 4 | 3 | 3 | 2 | 3 | 4 | 2 | 1 | 3 | 1 | 4 |
| 30 | 4 | 11.2 | 3 | 3 | 3 | 3 | 4 | 4 | 3 | 2 | 2 | 2 | 3 |
|  | 4 | 5.6 | 4 | 3 | 3 | 2 | 4 | 3 | 1 | 1 | 2 | 1 | 3 |
| 31 | 4 | 11.2 | 2 | 4 | 3 | 4 | 4 | 4 | 1 | 2 | 2 | 2 | 3 |
|  | 4 | 5.6 | 2 | 3 | 2 | 2 | 3 | 3 | 1 | 0 | 4 | 1 | 2 |
| 32 | 4 | 11.2 | 4 | 4 | 4 | 4 | 4 | 4 | 2 | 2 | 4 | 4 | 4 |
|  | 4 | 5.6 | 2 | 4 | 4 | 4 | 4 | 5 | 2 | 2 | 2 | 4 | 4 |
| 33 | 4 | 11.2 | 4 | 4 | 3 | 4 | 4 | 4 | 3 | 4 | 4 | 3 | 4 |
|  | 4 | 5.6 | 4 | * | 4 | 2 | 4 | 4 | 3 | 3 | 4 | 3 | 4 |
| 34 | 4 | 11.2 | 4 | 4 | 4 | 4 | 4 | 4 | 2 | 3 | 3 | 3 | 4 |
|  | 4 | 5.6 | 2 | 3 | 4 | 2 | 4 | 3 | 2 | 3 | 3 | 3 | 3 |
| 35 | 4 | 11.2 | 4 | 4 | 3 | 3 | 4 | 4 | 2 | 3 | 3 | 3 | 4 |
|  | 4 | 5.6 | 4 | 3 | 4 | 2 | 4 | 4 | 2 | 3 | 3 | 3 | 3 |
| 36 | 4 | 11.2 | 3 | 4 | 4 | 3 | 4 | 4 | 3 | 3 | 4 | 4 | 4 |
|  | 4 | 5.6 | 4 | 4 | 2 | 3 | 4 | 3 | 2 | 3 | 4 | 2 | 3 |
| 37 | 4 | 11.2 | 4 | 4 | 4 | 3 | 4 | 4 | 3 | 3 | 4 | 4 | 4 |
|  | 4 | 5.6 | 4 | 4 | 4 | 3 | 4 | 4 | 3 | 3 | 3 | 3 | 3 |
| 38 | 2 | 11.2 | 0 | 1 | 1 | 0 | 0 | 0 | 0 | 0 | 3 | 0 | 0 |
|  | 2 | 5.6 | 0 | 1 | 0 | 0 | 0 | 0 | 0 | 0 | 1 | 0 | 0 |
| 39 | 4 | 11.2 | 2 | 4 | 3 | 1 | 4 | 4 | 3 | 3 | 4 | 2 | 3 |
|  | 4 | 5.6 | 2 | 3 | 2 | 1 | 2 | 3 | 3 | 2 | 4 | 2 | 3 |
| 40 | 4 | 11.2 | 1 | 2 | 1 | 1 | 4 | 1 | 1 | 1 | 2 | 0 | 2 |
| 42 | 4 | 11.2 | 4 | 4 | 4 | 4 | 4 | 3 | 3 | 4 | 4 | 3 | 4 |
|  | 4 | 5.6 | 4 | 3 | 2 | 3 | 4 | 4 | 3 | 2 | 4 | 1 | 4 |

TABLE II

| Compound | WAT | kg H | L | M | N | O | P | B | Q | D | R | E | F | C | J | S | K | T |
|---|---|---|---|---|---|---|---|---|---|---|---|---|---|---|---|---|---|---|
| 1 | 4 | 5.6 | 4 | 2 | 2 | 3 | 3 | 3 | 1 | 1 | 1 | 3 | 3 | 3 | 2 | 2 | 3 | 3 |
|  | 4 | 1.12 | 2 | 1 | 1 | 1 | 2 | 2 | 1 1 | 1 | 2 | 2 | 2 |  | 2 | 3 | 3 |  |
|  | 4 | .28 | 1 | 1 | 0 | 1 | 1 | 1 | 1 | 1 | 0 | 2 | 2 | 1 | 0 | 1 | 1 | 1 |
| 2 | 4 | 5.6 | 4 | 3 | 2 | 3 | 3 | 3 | 4 | 2 | 4 | 4 | 4 | 3 | 3 | 4 | 3 | 3 |
|  | 4 | 1.12 | 2 | 1 | 1 | 1 | 1 | 2 | 1 | 1 | 1 | 2 | 2 | 2 | 1 | 1 | 2 | 2 |
|  | 2 | .28 | 1 | 0 | 0 | 0 | 1 | 1 | 0 | 0 | 0 | 0 | 0 | 1 | 0 | 0 | 0 | 1 |
| 3 | 4 | 5.6 | 3 | 3 | 4 | 4 | 3 | 3 | 4 | 2 | 3 | 4 | 4 | 1 | 2 | 2 | 2 | 2 |
|  | 4 | 1.12 | 2 | 1 | 1 | 1 | 2 | 2 | 1 | 1 | 1 | 2 | 1 | 1 | 2 | 2 | 2 | 2 |
|  | 4 | .28 | 1 | 0 | 0 | 0 | 1 | 1 | 0 | 1 | 0 | 1 | 0 | 0 | 0 | 1 | 1 | 1 |
| 4 | 4 | 5.6 | 4 | 3 | 2 | 3 | 3 | 3 | 1 | 2 | 2 | 4 | 4 | 3 | 1 | 3 | 3 | 3 |
|  | 4 | 1.12 | 2 | 1 | 1 | 1 | 3 | 2 | 1 | 1 | 1 | 3 | 2 | 2 | 1 | 1 | 1 | 2 |
|  | 4 | .28 | 1 | 0 | 1 | 0 | 1 | 1 | 1 | 1 | 0 | 2 | 0 | 0 | 0 | 0 | 0 | 0 |
| 5 | 4 | 4.48 | 4 | 3 | 3 | 3 | 4 | 4 | 3 | 4 | 4 | 4 | 4 | 4 | 4 | 4 | 4 | 4 |
|  | 4 | 1.12 | 1 | 1 | 1 | 2 | 3 | 2 | 2 | 2 | 2 | 3 | 3 | 3 | 3 | 4 | 3 | 4 |
|  | 4 | .224 | 1 | 0 | 1 | 0 | 3 | 2 | 1 | 2 | 0 | 2 | 0 | 1 | 1 | 3 | 3 | 3 |
| 6 | 4 | 1.12 | 2 | 1 | 1 | 3 | 4 | 2 | 1 | 2 | 4 | 4 | 4 | 4 | 4 | 4 | 4 | 4 |
|  | 4 | .28 | 1 | 1 | 1 | 1 | 3 | 1 | 1 | 2 | 2 | 2 | 2 | 2 | 1 | 3 | 2 | 3 |
|  | 4 | .056 | 1 | 0 | 0 | 0 | 1 | 1 | 0 | 1 | 1 | 0 | 1 | 0 | 0 | 1 | 1 | 2 |
| 7 | 4 | 1.12 | 0 | 0 | 0 | 0 | 1 | 2 | 0 | 4 | 0 | 0 | 0 | 0 | 0 | 0 | 0 | 0 |
| 8 | 4 | 1.12 | 1 | 1 | 1 | 1 | 2 | 2 | 1 | 1 | 0 | 2 | 3 | 2 | 1 | 0 | 1 | 4 |
| 9 | 4 | 5.6 | 4 | 3 | 2 | 3 | 3 | 3 | 3 | * | 4 | 4 | 4 | 4 | 3 | 4 | 4 | 4 |
|  | 4 | 1.12 | 2 | 2 | 2 | 3 | 3 | 3 | 1 | 2 | 4 | 4 | 4 | 4 | 2 | 4 | 3 | 4 |
|  | 4 | .28 | 1 | 1 | 1 | 1 | 2 | 2 | 1 | 2 | 2 | 2 | 2 | 2 | 1 | 2 | 2 | 2 |
| 10 | 4 | 5.6 | 3 | 3 | 2 | 4 | 4 | 3 | 4 | 4 | 4 | 4 | 4 | 4 | 4 | 4 | 4 | 4 |
|  | 4 | 1.12 | 2 | 3 | 2 | 3 | 3 | 2 | 2 | 3 | 2 | 4 | 4 | 2 | 2 | 4 | 3 | 4 |
|  | 4 | .28 | 1 | 1 |  | 1 | 1 | 1 | 2 | 1 | 1 | 4 | 2 | 2 | 0 | 2 | 1 | 2 |
| 13 | 4 | 4.48 | 3 | 3 | 3 | 3 | 3 | 3 | 3 | 3 | 3 | 4 | 3 | 4 | 3 | 4 | 3 | 3 |
|  | 4 | 1.12 | 1 | 2 | 1 | 2 | 2 | 3 | 2 | 2 | 2 | 3 | 1 | 1 | 2 | 4 | 3 | 3 |
|  | 4 | .224 | 1 | 0 | 0 | 2 | 2 | 1 | 1 | 1 | 1 | 3 | 1 | 1 | 1 | 4 | 2 | 3 |
| 14 | 4 | 5.6 | 3 | 3 | 3 | 3 | 3 | 2 | 1 | 4 | 4 | 4 | 4 | 2 | 4 | 4 | 4 |  |
|  | 4 | 1.12 | 2 | 2 | 1 | 2 | 2 | 2 | 0 | 2 | 4 | 3 | 3 | 2 | 1 | 2 | 3 | 4 |
| 15 | 4 | 1.12 | 1 | 0 | 0 | 0 | 3 | 2 | 0 | 1 | 0 | 2 | 1 | 1 | 2 | 2 | 1 | 3 |
| 16 | 4 | 5.6 | 2 | 1 | 1 | 2 | 3 | 3 | 1 | 2 | 2 | 2 | 4 | 1 | 0 | 2 | 2 | 3 |
|  | 4 | 1.12 | 1 | 1 | 1 | 1 | 3 | 2 | 1 | 1 | 1 | 3 | 2 | 1 | 0 | 2 | 1 | 2 |
|  | 4 | .28 | 1 | 0 | 0 | 0 | 1 | 1 | 0 | 1 | 1 | 1 | 1 | 0 | 0 | 0 | 0 | 0 |
| 17 | 4 | 5.6 | 2 | 1 | 4 | 4 | 4 | 3 | 1 | 2 | 2 | 4 | 4 | 3 | 3 | 4 | 4 | 4 |
|  | 4 | 1.12 | 2 | 0 | 1 | 2 | 4 | 3 | 1 | 2 | 2 | 4 | 3 | 2 | 2 | 2 | 2 | 4 |
|  | 4 | .28 | 1 | 1 | 1 | 1 | 2 | 1 | 0 | 1 | 0 | 2 | 1 | 1 | 1 | 1 | 1 | 2 |
| 18 | 4 | 5.6 | 2 | 2 | 3 | 3 | 4 | 2 | 2 | 2 | 1 | 4 | 4 | 1 | 3 | 3 | 3 | 4 |
|  | 4 | 1.12 | 1 | 1 | 1 | 1 | 3 | 2 | 1 | 1 | 1 | 3 | 2 | 1 | 1 | 2 | 2 | 3 |
| 19 | 4 | 5.6 | 3 | 1 | 1 | 4 | 3 | 3 | 2 | 2 | 3 | 4 | 4 | 1 | 4 | 3 | 4 | 4 |
|  | 4 | 1.12 | 1 | 1 | 1 | 1 | 3 | 2 | 1 | 1 | 1 | 2 | 2 | 1 | 0 | 3 | 1 | 3 |
|  | 4 | .28 | 1 | 0 | 0 | 0 | 1 | 1 | 0 | 0 | 0 | 1 | 1 | 0 | 0 | 1 | 1 | 1 |
| 20 | 4 | 5.6 | 1 | 2 | 3 | 4 | 4 | 2 | 4 | 2 | 2 | 3 | 4 | 3 | 3 | 4 | 4 | 4 |
|  | 4 | 1.12 | 1 | 1 | 1 | 1 | 2 | 1 | 1 | 1 | 4 | 4 | 2 | 1 | 2 | 2 | 2 | 3 |
| 21 | 4 | 5.6 | 2 | 1 | 1 | 3 | 3 | 2 | 1 | 1 | 1 | 2 | 2 | 1 | 1 | 2 | 2 | 3 |
|  | 4 | 1.12 | 1 | 2 | 1 | 1 | 2 | 1 | 0 | 1 | 0 | 1 | 1 | 0 | 1 | 1 | 1 |  |
| 22 | 4 | 5.6 | 3 | 3 | 2 | 4 | 3 | 1 | 1 | 4 | 4 | 4 | 4 | 3 | 4 | 4 | 4 |  |
|  | 4 | 1.12 | 1 | 1 | 1 | 1 | 3 | 2 | 1 | 1 | 2 | 4 | 3 | 2 | 1 | 3 | 2 | 3 |
|  | 4 | .28 | 1 | 0 | 1 | 1 | 2 | 1 | 1 | 1 | 1 | 2 | 1 | 1 | 0 | 1 | 1 | 2 |
| 23 | 4 | 5.6 | 3 | 2 | 3 | 3 | 4 | 4 | 1 | 3 | 2 | 4 | 4 | 3 | 3 | 4 | 3 | 4 |

TABLE II-continued

| Compound | WAT | kg H | L | M | N | O | P | B | Q | D | R | E | F | C | J | S | K | T |
|---|---|---|---|---|---|---|---|---|---|---|---|---|---|---|---|---|---|---|
|  | 4 | 1.12 | 2 | 1 | 1 | 2 | 3 | 2 | 1 | 2 | 2 | 4 | 4 | 2 | 1 | 4 | 2 | 4 |
|  | 4 | .28 | 1 | 1 | 1 | 0 | 1 | 1 | 0 | 1 | 1 | 4 | 2 | 1 | 0 | 1 | 1 | 2 |
| 24 | 4 | 5.6 | 4 | 4 | 2 | 4 | 4 | 4 | 2 | 4 | 3 | 4 | 4 | 4 | 3 | 4 | 4 | 4 |
|  | 4 | 1.12 | 2 | 1 | 1 | 3 | 4 | 2 | 1 | 2 | 3 | 4 | 4 | 2 | 1 | 4 | 4 | 4 |
|  | 4 | .28 | 1 | 0 | 0 | 1 | 2 | 1 | 0 | 1 | 1 | 4 | 2 | 1 | 0 | 1 | 1 | 2 |
| 25 | 4 | 5.6 | 3 | 3 | 2 | 4 | 4 | 3 | 1 | 4 | 3 | 4 | 4 | 4 | 4 | 4 | 4 | 4 |
|  | 4 | 1.12 | 1 | 1 | 1 | 3 | 3 | 2 | 1 | 2 | 2 | 4 | 3 | 3 | 1 | 3 | 2 | 3 |
|  | 4 | .28 | 1 | 0 | 0 | 0 | 2 | 1 | 0 | 1 | 2 | 3 | 2 | 1 | 0 | 1 | 1 | 2 |
|  | 4 | 5.6 | 4 | 3 | 4 | 4 | 3 | 2 | 4 | 4 | 4 | 4 | 4 | 3 | 4 | 4 | 4 |  |
|  | 4 | 1.12 | 2 | 1 | 1 | 3 | 3 | 2 | 1 | 2 | 2 | 4 | 4 | 4 | 2 | 4 | 4 | 4 |
|  | 4 | .28 | 1 | 1 | 1 | 1 | 2 | 2 | 1 | 2 | 1 | 2 | 2 | 2 |  | 4 | 3 | 3 |
| 27 | 4 | 5.6 | 4 | 4 | 3 | 4 | 4 | 3 | 2 | 4 | 3 | 4 | 4 | 4 | 4 | 4 | 4 | 4 |
|  | 4 | 1.12 | 2 | 1 | 1 | 1 | 3 | 2 | 2 | 2 | 2 | 3 | 3 | 2 | 2 | 4 | 3 | 4 |
|  | 4 | .28 | 2 | 0 | 0 | 0 | 2 | 1 | 1 | 1 | 1 | 2 | 2 | 2 | 1 | 2 | 2 | 2 |
| 28 | 4 | 5.6 | 3 | 4 | 3 | 3 | 4 | 3 | 2 | 4 | 3 | 4 | 4 | 4 | 4 | 4 | 4 | 4 |
|  | 4 | 1.12 | 2 | 1 | 1 | 2 | 4 | 3 | 2 | 3 | 3 | 4 | 4 | 2 | 2 | 4 | 3 | 3 |
|  | 4 | .28 | 1 | 0 | 1 | 1 | 2 | 2 | 1 | 1 | 2 | 2 | 2 | 2 | 1 | 2 | 2 | 2 |
| 29 | 4 | 5.6 | 4 | 4 | 4 | 3 | 3 | 4 | 1 | 4 | 3 | 4 | 4 | 4 | 4 | 4 | 4 | 4 |
|  | 4 | 1.12 | 2 | 2 | 1 | 2 | 3 | 2 | 1 | 2 | 2 | 4 | 4 | 2 | 2 | 3 | 3 | 4 |
|  | 4 | .28 | 1 | 0 | 1 | 1 | 2 | 1 | 1 | 1 | 2 | 2 | 2 | 1 | 0 | 2 | 2 | 2 |
| 30 | 4 | 5.6 | 4 | 4 | 2 | 4 | 4 | 4 | 4 | 4 | 4 | 4 | 4 | 4 | 4 | 4 | 4 | 4 |
|  | 4 | 1.12 | 1 | 1 | 1 | 1 | 2 | 1 | 1 | 2 | 2 | 4 | 4 | 4 | 1 | 2 | 2 | 4 |
|  | 4 | .28 | 1 | 1 | 1 | 1 | 2 | 1 | 1 | 1 | 2 | 2 | 2 | 2 | 0 | 2 | 2 | 2 |
| 31 | 4 | 5.6 | 3 | 3 | 2 | 2 | 3 | 3 | 1 | 3 | 3 | 4 | 4 | 4 | 4 | 4 | 4 | 4 |
|  | 4 | 1.12 | 2 | 3 | 1 | 1 | 4 | 4 | 2 | 2 | 2 | 4 | 4 | 4 | 3 | 3 | 3 | 3 |
|  | 4 | .28 | 1 | 0 | 0 | 1 | 2 | 1 | 1 | 1 | 1 | 3 | 2 | 1 | 1 | 1 | 1 | 2 |
| 32 | 4 | 5.6 | 4 | 4 | 3 | 4 | 4 | 4 | 2 | 3 | 4 | 4 | 4 | 4 | 4 | 4 | 4 | 4 |
|  | 4 | 1.12 | 2 | 1 | 1 | 1 | 2 | 3 | 1 | 1 | 4 | 3 | 2 | 3 | 1 | 2 | 3 | 3 |
|  | 4 | .28 | 1 | 1 | 0 | 1 | 1 | 1 | 0 | 0 | 1 | 1 | 1 | 1 | 0 | 1 | 2 | 2 |
| 33 | 4 | 5.6 | 2 | 3 | 2 | 4 | 4 | 3 | 1 | 2 | 1 | 4 | 4 | 3 | 4 | 4 | 4 | 3 |
|  | 4 | 1.12 | 0 | 2 | 1 | 1 | 4 | 2 | 1 | 1 | 0 | 2 | 1 | 1 | 1 | 1 | 1 | 2 |
|  | 4 | .28 | 1 | 1 | 0 | 0 | 2 | 1 | 0 | 1 | 0 | 1 | 1 | 0 | 0 | 0 | 0 | 2 |
| 34 | 4 | 5.6 | 3 | 3 | 3 | 4 | 4 | 4 | 2 | 2 | 2 | 4 | 2 | 1 | 3 | 4 | 4 | 4 |
|  | 4 | 1.12 | 2 | 1 | 1 | 0 | 4 | 3 | 1 | 1 | 1 | 4 | 2 | 1 | 2 | 2 | 2 | 2 |
|  | 4 | .28 | 1 | * | 0 | 0 | 2 | 1 | 1 | 1 | 1 | 1 | 1 | 0 | 0 | 1 | 1 | 1 |
| 35 | 4 | 5.6 | 2 | 2 | 1 | 4 | 4 | 3 | 2 | 2 | 2 | 4 | 4 | 2 | 2 | 4 | 3 | 4 |
|  | 4 | 1.12 | 1 | 2 | 1 | 1 | 2 | 2 | 1 | 1 | 1 | 3 | 2 | 1 | 1 | 2 | 2 | 2 |
|  | 2 | .28 | 1 | 0 | 0 | 0 | 1 | 0 | 0 | 0 | 0 | 0 | 0 | 0 | 1 | 0 | 0 |  |
| 36 | 4 | 5.6 | 3 | 2 | 3 | 3 | 4 | 3 | 3 | 2 | 2 | 3 | 4 | 3 | 3 | 3 | 3 | 4 |
|  | 4 | 1.12 | 1 | 1 | 1 | 1 | 2 | 2 | 1 | 2 | 1 | 2 | 1 | 1 | 1 | 1 | 2 | 2 |
|  | 4 | .28 | 1 | 0 | 0 | 1 | 1 | 1 | 0 | 1 | 1 | 1 | 0 | 0 | 1 | 0 | 0 | 1 |
| 37 | 4 | 5.6 | 3 | 1 | 1 | 3 | 4 | 3 | 1 | 2 | 1 | 4 | 3 | 2 | 1 | 3 | 3 | 4 |
|  | 4 | 1.12 | 1 | 1 | 1 | 1 | 3 | 2 | 1 | 1 | 0 | 2 | 2 | 1 | 1 | 2 | 3 | 3 |
|  | 4 | .28 | 1 | 0 | 1 | 1 | 3 | 2 | 1 | 1 | 0 | 2 | 1 | 0 | 1 | 1 | 2 | 2 |
| 39 | 4 | 5.6 | 2 | 3 | 3 | 4 | 4 | 3 | 4 | 2 | 2 | 4 | 4 | 3 | 3 | 4 | 4 | 3 |
|  | 4 | 1.12 | 1 | 2 | 1 | 1 | 2 | 1 | 1 | 2 | 1 | 2 | 4 | 1 | 1 | 2 | 2 | 3 |
|  | 4 | .28 | 1 | 0 | 1 | 0 | 1 | 1 | 0 | 1 | 0 | 2 | 1 | 1 | 0 | 1 | 1 | 2 |
| 42 | 4 | 5.6 | 3 | 4 | 2 | 4 | 3 | 4 | 4 | 4 | 4 | 4 | 4 | 4 | 2 | 4 | 4 | 4 |
|  | 4 | 1.12 | 1 | 1 | 1 | 1 | 3 | 3 | 1 | 2 | 2 | 4 | 4 | 1 | 1 | 3 | 3 | 3 |
|  | 4 | .28 | 1 | 0 | 0 | 0 | 1 | 1 | 1 | 1 | 1 | 3 | 3 | 1 | 1 | 1 | 1 | 3 |

EXAMPLE 48

The pre-emergent herbicidal activity of various compounds of this invention is demonstrated as follows. A good grade of top soil is placed in aluminum pans and compacted to a depth of three-eighth to one-half inch from the top of each pan. A predetermined number of seeds or vegetative propagules of each of several plant species are placed on top of the soil in each pan and then pressed down. Herbicidal compositions (as described in Example 47) employing the active ingredients of this invention are applied by admixture with or incorporation in the top layer of soil.

In this method, the soil required to cover the seeds and propagules is weighed and admixed with a herbicidal composition containing a known amount of active ingredient. The pans are then filled with the admixture and leveled. Watering is carried out by permitting the soil in the pans to absorb moisture through apertures in the pan bottoms. The seed and propagule containing pans are placed on a wet sand bench and maintained for approximately 2 weeks under ordinary conditions of sunlight and watering. At the end of this period the number of emerged plants of each species is noted and compared to an untreated control. The data is given in Table III.

The pre-emergent herbicidal activity index used below is based upon the average percent control of each species as follows:

| Percent Control | Index |
|---|---|
| 0 – 25% | 0 |
| 26 – 50% | 1 |
| 51 – 75% | 2 |
| 76 – 100% | 3 |

Plant species are identified in Table III by the same code letters used in Example 47.

TABLE III

| Compound | kg h | A | B | C | D | E | F | G | H | I | J | K |
|---|---|---|---|---|---|---|---|---|---|---|---|---|
| 1 | 11.2 | 3 | 0 | 0 | 0 | 0 | 0 | 0 | 0 | 0 | 0 | 0 |
| 2 | 11.2 | 2 | 0 | 0 | 0 | 0 | 1 | 0 | 3 | 0 | 0 | 0 |
| 3 | 11.2 | 3 | 0 | 0 | 1 | 0 | 1 | 1 | 0 | 0 | 0 | 0 |
| 4 | 11.2 | 2 | 0 | 0 | 0 | 0 | 0 | 0 | 0 | 0 | 0 | 0 |
| 5 | 11.2 | 3 | 0 | 3 | 0 | 1 | 0 | 0 | 1 | 2 | 1 | 0 |
| 6 | 11.2 | 1 | 0 | 0 | 0 | 0 | 0 | 0 | 0 | 0 | 0 | 0 |
| 7 | 11.2 | 1 | 0 | 0 | 0 | 0 | 0 | 0 | 0 | 0 | 0 | 0 |
| 8 | 11.2 | 1 | 0 | 0 | 0 | 0 | 0 | 0 | 1 | 0 | 0 | 0 |
| 9 | 11.2 | 3 | 0 | 0 | 0 | 0 | 1 | 1 | 0 | 0 | 0 | 0 |
| 10 | 11.2 | 3 | 0 | 0 | 0 | 0 | 0 | 0 | 0 | 0 | 0 | 0 |
| 11 | 11.2 | 3 | 0 | 0 | 0 | 0 | 0 | 0 | 0 | 0 | 0 | 0 |
| 12 | 11.2 | 1 | 0 | 0 | 0 | 0 | 0 | 0 | 0 | 0 | 0 | 0 |
| 13 | 11.2 | 2 | 0 | 0 | 3 | 3 | 0 | 0 | 1 | 0 | 0 |  |
| 14 | 11.2 | 3 | 0 | 0 | 3 | 0 | 0 | 0 | 1 | 0 | 1 |  |
| 15 | 11.2 | 0 | 0 | 0 | 0 | 0 | 0 | 0 | 0 | 0 | 0 | 0 |
| 16 | 11.2 | 0 | 0 | 0 | 0 | 0 | 0 | 0 | 0 | 0 | 0 | 0 |

TABLE III-continued

| Compound | kg h | Plant Species | | | | | | | | | | |
|---|---|---|---|---|---|---|---|---|---|---|---|
| | | A | B | C | D | E | F | G | H | I | J | K |
| 17 | 11.2 | 1 | 0 | 0 | 0 | 0 | 0 | 0 | 0 | 0 | 0 | 0 |
| 18 | 11.2 | 0 | 0 | 0 | 0 | 0 | 0 | 0 | 0 | 0 | 0 | 0 |
| 19 | 11.2 | 1 | 0 | 0 | 0 | 0 | 0 | 0 | 0 | 0 | 0 | 0 |
| 20 | 11.2 | 0 | 0 | 0 | 0 | 0 | 0 | 0 | 0 | 0 | 0 | 0 |
| 21 | 11.2 | 2 | 0 | 0 | 0 | 0 | 0 | 0 | 0 | 0 | 0 | 0 |
| 22 | 11.2 | 2 | 0 | 0 | 0 | 0 | 0 | 1 | 1 | 0 | 0 | 0 |
| 23 | 11.2 | 3 | 0 | 0 | 0 | 3 | 1 | 0 | 0 | 0 | 0 | 0 |
| 24 | 11.2 | 1 | 0 | 0 | 0 | 0 | 0 | 0 | 1 | 0 | 0 | 0 |
| 25 | 11.2 | 2 | 0 | 0 | 0 | 0 | 0 | 0 | 0 | 0 | 0 | 0 |
| 26 | 11.2 | 2 | 0 | 0 | 0 | 0 | 0 | 0 | 0 | 0 | 0 | 0 |
| 27 | 11.2 | 2 | 0 | 0 | 1 | 0 | 0 | 1 | 0 | 0 | 0 | 0 |
| 28 | 11.2 | 1 | 0 | 0 | 0 | 0 | 0 | 0 | 0 | 0 | 0 | 0 |
| 29 | 11.2 | 2 | 0 | 0 | 0 | 0 | 0 | 0 | 0 | 0 | 0 | 0 |
| 30 | 11.2 | 2 | 0 | 0 | 1 | 0 | 0 | 0 | 1 | 1 | 0 | 0 |
| 31 | 11.2 | 2 | 0 | 0 | 0 | 0 | 0 | 0 | 0 | 0 | 0 | 0 |
| 32 | 11.2 | 3 | 0 | 0 | 0 | 0 | 0 | 0 | 0 | 0 | 0 | 0 |
| 33 | 11.2 | 3 | 0 | 0 | 0 | 0 | 0 | 0 | 1 | 0 | 0 | 0 |
| 34 | 11.2 | 3 | 0 | 0 | 1 | 0 | 0 | 0 | 0 | 1 | 0 | 0 |
| 35 | 11.2 | 3 | 0 | 0 | 0 | 0 | 0 | 2 | 2 | 3 | 0 | 0 |
| 36 | 11.2 | 3 | 0 | 0 | 0 | 0 | 0 | 1 | 1 | 0 | 0 | 0 |
| 37 | 11.2 | 3 | 0 | 0 | 0 | 1 | 0 | 0 | 1 | 0 | 0 | 0 |
| 38 | 11.2 | 0 | 0 | 0 | 0 | 0 | 0 | 0 | 0 | 0 | 0 | 0 |
| 39 | 11.2 | 3 | 0 | 0 | 0 | 0 | 0 | 0 | 0 | 0 | 0 | 0 |
| 40 | 11.2 | 0 | 0 | 0 | 0 | 0 | 0 | 0 | 1 | 1 | 0 | 0 |
| 42 | 11.2 | 3 | 0 | 0 | 0 | 0 | 0 | 0 | 0 | 0 | 0 | 0 |

From the test results presented in Tables I and II, it can be seen that the post-emergent herbicidal activity of the compounds of this invention is, for the most part, general in nature. In certain specific instances, however, some selectivity is demonstrated. On the other hand, the test results showing pre-emergent herbicidal activity clearly show the selectivity of action on Canada Thistle and a few other species. In this regard it should be recognized that each individual species selected for the above tests is a representative member of a recognized family of plant species.

The herbicidal compositions, including concentrates which require dilution prior to application to the plants, of this invention contain from 5 to 95 parts by weight of at least one active ingredient and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, all parts being by weight of the total composition. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

Water dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible powder of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform and usually contains from 5 to about 95 parts by weight active ingredient, from about 0.25 to 25 parts by weight dispersant, and from about 4.5 to 94.5 parts by weight of water.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface active agent and about 4 to 94 parts solvent, all parts being by weight based on the total weight of emulsifiable oil.

Although compositions of this invention can also contain other additaments, for example, fertilizers, phytotoxicants and plant growth regulatns, pesticides and the like used as adjuvants or in combination with any of the above-described adjuvants, it is preferred to employ the compositions of this invention alone with sequential treatments with the other phytotoxicants, fertilizers and the like for maximum effect. For example, the field could be sprayed with a composition of this invention either before or after being treated with fertilizers, other phytotoxicants and the like. The compositions of this invention can also be admixed with the other materials, e.g., fertilizers, other phytotoxicants, etc., and applied in a single application. Chemicals useful in combination with the active ingredients of this invention either simultaneously or sequentially include, for example, triazines, ureas, carbamates, acetamides, acetanilides, uracils, acetic acids, phenols, thiolcarbamates, triazoles, benzoic acids, nitriles and the like.

Fertilizers useful in combination with the active ingredients include, for example, ammonium nitrate, urea, potash, and superphosphate.

When operating in accordance with the present invention, effective amounts of the glycinonitriles are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 22.4 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although the invention is described with respect to specific modifications, the details thereof are not to be construed as limitations except to the extent indicated in the following claims.

What is claimed is:

1. A compound of the formula

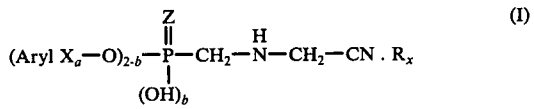

(I)

wherein Aryl is selected from phenyl, naphthyl or biphenylyl, each X is a substituent on said Aryl selected from halogen, alkyl of 1 to 4 carbons, alkoxy and alkylthio of 1 to 3 carbons, alkoxycarbonyl of 2 to 3 carbon atoms, methylenedioxy, cyano, trifluoromethyl or nitro, Z is oxygen or sulfur, $a$ is an integer from zero to 3, $b$ is an integer from zero to 1, R is a strong acid capable of forming a salt with the amino group, and $x$ is zero or 1, provided that $x$ must be zero when $b$ is 1.

2. A compound as defined in claim 1 wherein $a$ is zero.

3. A compound as defined in claim 1 wherein $x$ is one and $b$ is zero.

4. A compound as defined in claim 1 wherein $x$ is zero and $b$ is one.

5. A compound as defined in claim 1 wherein both $b$ and $x$ are zero.

6. A compound as defined in claim 1 wherein the strong acid has a pKa in water of 2.5 or less.

7. A compound as defined in claim 1 wherein Aryl is phenyl and Z is oxygen.

8. A compound as defined in claim 7 wherein $x$ is one and $b$ is zero.

9. A compound as defined in claim 7 wherein $x$ is zero and $b$ is one.

10. A compound as defined in claim 7 wherein both $b$ and $x$ are zero.

11. A compound as defined in claim 1 which is O,O-diphenyl N-phosphonomethylglycinonitrile.

12. A compound as defined in claim 1 which is O,O-di(p-methoxyphenyl) N-phosphonomethylglycinonitrile.

13. A compound as defined in claim 1 which is O,O-di(p-fluorophenyl) N-phosphonomethylglycinonitrile.

14. A compound as defined in claim 1 which is O-phenyl N-phosphonomethylglycinonitrile.

15. A compound as defined in claim 1 which is O-m-nitrophenyl N-phosphonomethylglycinonitrile.

16. A compound as defined in claim 1 which is O-o-chlorophenyl N-phosphonomethylglycinonitrile.

17. A compound as defined in claim 1 which is the hydrogen bromide salt of O,O-diphenyl N-phosphonomethylglycinonitrile.

18. A compound as defined in claim 1 which is the trifluoroacetic acid salt of O,O-diphenyl N-phosphonomethylglycinonitrile.

19. A compound as defined in claim 1 which is the methanesulfonic acid salt of O,O-diphenyl N-phosphonomethylglycinonitrile.

20. A herbicidal composition comprising a herbicidally effective amount of a compound of claim 1 and an inert diluent.

21. A herbicidal composition comprising a herbicidally effective amount of a compound of claim 2 and an inert diluent.

22. A herbicidal composition comprising a herbicidally effective amount of a compound of claim 3 and an inert diluent.

23. A herbicidal composition comprising a herbicidally effective amount of a compound of claim 4 and an inert diluent.

24. A herbicidal composition comprising a herbicidally effective amount of a compound of claim 5 and an inert diluent.

25. A herbicidal composition comprising a herbicidally effective amount of a compound of claim 6 and an inert diluent.

26. A herbicidal composition comprising a herbicidally effective amount of a compound of claim 7 and an inert diluent.

27. A herbicidal composition comprising a herbicidally effective amount of a compound of claim 8 and an inert diluent.

28. A herbicidal composition comprising a herbicidally effective amount of a compound of claim 9 and an inert diluent.

29. A herbicidal composition comprising a herbicidally effective amount of a compound of claim 10 and an inert diluent.

30. A herbicidal composition comprising a herbicidally effective amount of the compound of claim 11 and an inert diluent.

31. A herbicidal composition comprising a herbicidally effective amount of the compound of claim 12 and an inert diluent.

32. A herbicidal composition comprising a herbicidally effective amount of the compound of claim 13 and an inert diluent.

33. A herbicidal composition comprising a herbicidally effective amount of the compound of claim 14 and an inert diluent.

34. A herbicidal composition comprising a herbicidally effective amount of the compound of claim 15 and an inert diluent.

35. A herbicidal composition comprising a herbicidally effective amount of the compound of claim 16 and an inert diluent.

36. A herbicidal composition comprising a herbicidally effective amount of the compound of claim 17 and an inert diluent.

37. A herbicidal composition comprising a herbicidally effective amount of the compound of claim 18 and an inert diluent.

38. A herbicidal composition comprising a herbicidally effective amount of the compound of claim 19 and an inert diluent.

39. A herbicidal method which comprises contacting a plant or the plant growth medium with a herbicidally effective amount of a compound of claim 1.

40. A herbicidal method which comprises contacting a plant or the plant growth medium with a herbicidally effective amount of a compound of claim 2.

41. A herbicidal method which comprises contacting a plant or the plant growth medium with a herbicidally effective amount of a compound of claim 3.

42. A herbicidal method which comprises contacting a plant or the plant growth medium with a herbicidally effective amount of a compound of claim 4.

43. A herbicidal method which comprises contacting a plant or the plant growth medium with a herbicidally effective amount of a compound of claim 5.

44. A herbicidal method which comprises contacting a plant or the plant growth medium with a herbicidally effective amount of a compound of claim 6.

45. A herbicidal method which comprises contacting a plant or the plant growth medium with a herbicidally effective amount of a compound of claim 7.

46. A herbicidal method which comprises contacting a plant or the plant growth medium with a herbicidally effective amount of a compound of claim 8.

47. A herbicidal method which comprises contacting a plant or the plant growth medium with a herbicidally effective amount of a compound of claim 9.

48. A herbicidal method which comprises contacting a plant or the plant growth medium with a herbicidally effective amount of a compound of claim 10.

49. A herbicidal method which comprises contacting a plant or the plant growth medium with a herbicidally effective amount of the compound of claim 11.

50. A herbicidal method which comprises contacting a plant or the plant growth medium with a herbicidally effective amount of the compound of claim 12.

51. A herbicidal method which comprises contacting a plant or the plant growth medium with a herbicidally effective amount of the compound of claim 13.

52. A herbicidal method which comprises contacting a plant or the plant growth medium with a herbicidally effective amount of the compound of claim 14.

53. A herbicidal method which comprises contacting a plant or the plant growth medium with a herbicidally effective amount of the compound of claim 15.

54. A herbicidal method which comprises contacting a plant or the plant growth medium with a herbicidally effective amount of the compound of claim 16.

55. A herbicidal method which comprises contacting a plant or the plant growth medium with a herbicidally effective amount of the compound of claim 17.

56. A herbicidal method which comprises contacting a plant or the plant growth medium with a herbicidally effective amount of the compound of claim 18.

57. A herbicidal method which comprises contacting a plant or the plant growth medium with a herbicidally effective amount of the compound of claim 19.

* * * * *

UNITED STATES PATENT AND TRADEMARK OFFICE
CERTIFICATE OF CORRECTION

PATENT NO. : 4,067,719
DATED : January 10, 1978
INVENTOR(S) : Gerard A. Dutra

It is certified that error appears in the above-identified patent and that said Letters Patent are hereby corrected as shown below:

In Table I, columns 16 and 17, two lines of ratings are incorrect for all plant species. The headings for Table I are shown below with the correct ratings.

| | | | Plant Species | | | | | | | | | | |
|---|---|---|---|---|---|---|---|---|---|---|---|---|---|
| Compound | WAT | $\frac{kg}{h}$ | A | B | C | D | E | F | G | H | I | J | K |
| 13 | 4 | 11.2 | 2 | * | 4 | 4 | 4 | 3 | 3 | 3 | 4 | 3 | 4 |
| 27 | 4 | 11.2 | 2 | 3 | 3 | 2 | 4 | 4 | 1 | 1 | 1 | 3 | 3 |

In Table II, columns 17 through 20, several lines of ratings are incorrect for many plant species. In addition, the Compound designation "26" should be inserted at the far left of the ninth line of ratings in the portion of Table II in columns 19 and 20. The headings for Table II are shown below with the correct ratings.

UNITED STATES PATENT AND TRADEMARK OFFICE
CERTIFICATE OF CORRECTION

PATENT NO. : 4,067,719
DATED : January 10, 1978
INVENTOR(S) : Gerard A. Dutra

It is certified that error appears in the above-identified patent and that said Letters Patent are hereby corrected as shown below:

Plant Species

| Compound | WAT | kg/h | L | M | N | O | P | B | Q | D | R | E | F | C | J | S | K | T |
|----------|-----|------|---|---|---|---|---|---|---|---|---|---|---|---|---|---|---|---|
| 1  | 4 | 1.12 | 2 | 1 | 1 | 1 | 2 | 2 | 1 | 1 | 1 | 2 | 2 | 2 | 1 | 2 | 3 | 3 |
| 3  | 4 | 5.6  | 3 | 3 | 4 | 4 | 3 | 3 | 4 | 2 | 3 | 4 | 4 | 1 | 3 | 3 | 3 | 4 |
| 14 | 4 | 5.6  | 3 | 3 | 3 | 3 | 3 | 2 | 1 | 2 | 4 | 4 | 4 | 2 | 4 | 4 | 4 | 4 |
| 21 | 4 | 1.12 | 1 | 2 | 1 | 1 | 1 | 1 | 0 | 1 | 0 | 1 | 1 | 1 | 0 | 1 | 1 | 1 |
| 22 | 4 | 5.6  | 3 | 3 | 2 | 4 | 4 | 3 | 1 | 1 | 4 | 4 | 4 | 3 | 4 | 4 | 4 | 4 |
| 26 | 4 | 5.6  | 4 | 3 | 4 | 4 | 4 | 3 | 2 | 4 | 4 | 4 | 4 | 3 | 4 | 4 | 4 | 4 |
| 28 | 4 | 1.12 | 2 | 1 | 1 | 2 | 3 | 2 | 1 | 2 | 2 | 3 | 3 | 2 | 2 | 4 | 3 | 3 |

In column 9, line 65, "while" should be -- white --.

In column 14, line 14, "3,4-meth-" should be -- 3,4-methy- --.

In column 16, Table I, in the line of ratings for Compound 17 at 11.2 kg/h, the rating under plant species I should be -- 4 --, and the rating under plant species J should be -- 3 --.

UNITED STATES PATENT AND TRADEMARK OFFICE
CERTIFICATE OF CORRECTION

PATENT NO. : 4,067,719
DATED : January 10, 1978
INVENTOR(S) : Gerard A. Dutra

It is certified that error appears in the above-identified patent and that said Letters Patent are hereby corrected as shown below:

In column 17, Table I, in the line of ratings for Compound 32 at 5.6 kg/h, the rating under plant species F should be -- 4 --.

In column 17, Table I, in the line of ratings for Compound 39 at 5.6 kg/h, the rating under plant species F should be -- 2 --.

In columns 17 and 18, Table II, in the line of ratings for Compound 10 at .28 kg/h, the rating under plant species N should be -- 1 --.

In column 7, line 3, "O,O-di)p-biphenylyl)" should read -- O,O-di(p-biphenylyl) --.

In columns 17 and 18, Table II, in the line of ratings for Compound 13 at 4.48 kg/h, the rating under plant species T should be -- 4 --.

In columns 17 and 18, Table II, in the line of ratings for Compound 20 at 5.6 kg/h, the rating under plant species E should be -- 4 --.

In columns 19 and 20, Table II, in the line of ratings for Compound 23 at 1.12 kg/h, the rating under plant species S should be -- 3 --.

UNITED STATES PATENT AND TRADEMARK OFFICE
CERTIFICATE OF CORRECTION

PATENT NO. : 4,067,719
DATED : January 10, 1978
INVENTOR(S) : Gerard A. Dutra

It is certified that error appears in the above-identified patent and that said Letters Patent are hereby corrected as shown below:

In columns 19 and 20, Table II, in the line of ratings for Compound 26 at .28 kg/h, the rating under plant species J should be - - 1 - -.

In columns 19 and 20, Table II, in the line of ratings for Compound 37 at 1.12 kg/h, the rating under plant species E should be - - 3 - -.

In columns 19 and 20, Table II, in the line of ratings for Compound 39 at 1.12 kg/h, the rating under plant species F should be - - 3 - -.

Signed and Sealed this

Sixth Day of June 1978

[SEAL]

Attest:

RUTH C. MASON
Attesting Officer

DONALD W. BANNER
Commissioner of Patents and Trademarks